(12) United States Patent
Cipra

(10) Patent No.: US 7,690,265 B2
(45) Date of Patent: Apr. 6, 2010

(54) CONSTANT MOMENT TESTING DEVICE FOR ELONGATED MEMBERS

(75) Inventor: Dale O. Cipra, Chatsworth, CA (US)

(73) Assignee: Pratt & Whitney Rocketdyne, Inc., Canoga Park, CA (US)

( * ) Notice: Subject to any disclaimer, the term of this patent is extended or adjusted under 35 U.S.C. 154(b) by 97 days.

(21) Appl. No.: 11/683,078

(22) Filed: Mar. 7, 2007

(65) Prior Publication Data

US 2008/0216585 A1  Sep. 11, 2008

(51) Int. Cl.
*G01N 3/00* (2006.01)

(52) U.S. Cl. .......................................... 73/851; 73/849

(58) Field of Classification Search ............ 73/851–853
See application file for complete search history.

(56) References Cited

U.S. PATENT DOCUMENTS

| | | | | |
|---|---|---|---|---|
| 4,958,522 A | * | 9/1990 | McKinlay | 73/847 |
| 4,986,132 A | * | 1/1991 | Calomino | 73/852 |
| 5,231,882 A | | 8/1993 | Bertele et al. | |
| 5,736,646 A | | 4/1998 | Dickinson et al. | |
| 5,789,682 A | | 8/1998 | Dickinson et al. | |
| 6,053,052 A | * | 4/2000 | Starostovic | 73/851 |
| 6,381,546 B1 | | 4/2002 | Starostovic | |
| 6,505,129 B2 | | 1/2003 | Starostovic et al. | |
| 6,668,231 B2 | | 12/2003 | Stylios | |
| 6,931,942 B2 | | 8/2005 | Uhlik et al. | |
| 7,201,064 B2 | * | 4/2007 | Doak et al. | 73/849 |
| 7,302,860 B1 | * | 12/2007 | Uhlik et al. | 73/853 |

OTHER PUBLICATIONS http://www.rumul.ch/320_e_vierpunkt.htm, Feb. 12, 2007.
http://www.deben.co.uk/details.php?id=15, Feb. 12, 2007.
http://www.tappi.org/s_tappi/doc_bookstore.asp?CID=7373 &DID=517357, Feb. 12, 2007.
http://www.metengr.com/Bend.htm, Feb. 12, 2007.
http://jsm.sagepub.com/cgo/content/abstract/, Feb. 12, 2007.
http://www.instron.us/wa/applications/ceramics/testing. aspx?ref=http://google.com/search, Feb. 12, 2007.
"Issues in four-point bend testing for assessing stress corrosion cracking susceptibility of welds," Bill Nimmo, Aeronwen Griffiths, Louise Crocker, Richard Shaw and Alan Turnbull; NPL Report MATC(A) 153, Nov. 2003.
http://books.google.com/books?id=HrbXUPRgSQ4C&pg=RA14-PA1&lpg=RA14-PA1&dq=four+point+bending+testing+machine &source=web&ots=S55NN1Gvku&sig=KoWRuy4Sl1gBYfQ-8lpZdrgvZEE#PRA14-PA1,M1; Orthodontic Materials: Scientific and Clinical Aspects; William A. Brantley and Theodore Eliades, 2001.

* cited by examiner

*Primary Examiner*—Lisa M Caputo
*Assistant Examiner*—Freddie Kirkland, III
(74) *Attorney, Agent, or Firm*—Carlson, Gaskey & Olds PC

(57) ABSTRACT

A testing device applies a load controlled bending moment which is constant along a length of an elongated member. The testing device also includes a drive system which rotates the elongated member while the bending load is applied to rapidly find defects which may only appear at a particular rotational position to determine whether the bending stiffness is uniform about the entire diameter of the elongated member.

15 Claims, 3 Drawing Sheets

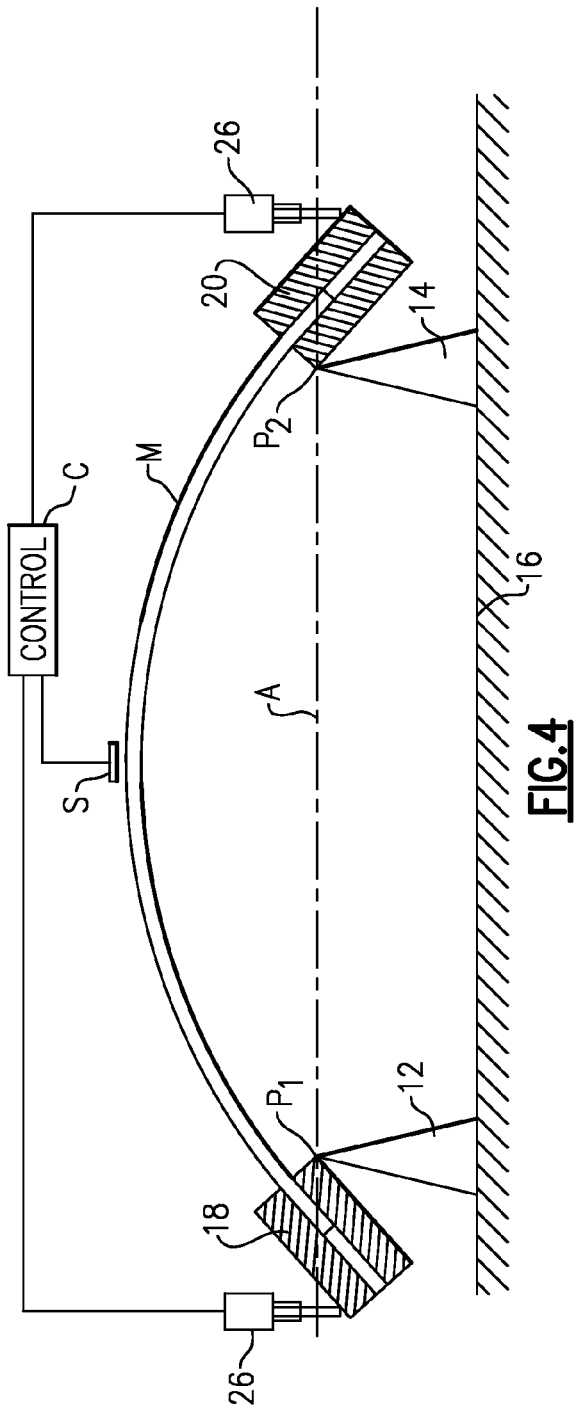
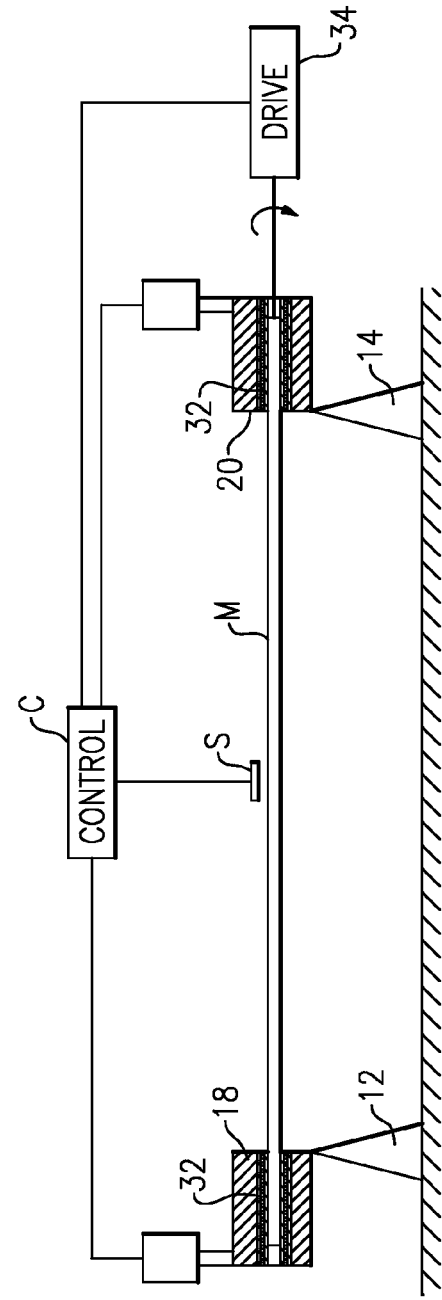

CONSTANT MOMENT TESTING DEVICE FOR ELONGATED MEMBERS

BACKGROUND OF THE INVENTION

The present invention relates to a structural testing device, and more particularly to a load controlled bending moment testing device which applies a constant moment along an elongated member.

Conventional structural testing is often performed with a three-point or four-point testing device as illustrated in FIG. 1A. Performing such structural tests on elongated members may be complicated as the elongated member tends to buckle at the discrete location of load application. In the case of thin hollow-walled shaft members, the concentrated shear loads (FIG. 1B) from such point bending testing may also cause local damage while generally under predicting the actual strength of the shaft.

Additionally, conventional point testing does not apply a constant bending moment along the entire length of the elongated member. Should the testing be structured as proof testing to eliminate flawed members, such testing may not eliminate all flawed members since a length ramped portion in FIG. 1C of the elongated member may not be subjected to the desired proof bending stress (FIG. 1C).

Accordingly, it is desirable to provide a structural testing device which determines nominal strength of an elongated member through application of a constant moment along the length of the elongated member without application of concentrated shear loads directly to the member.

SUMMARY OF THE INVENTION

The testing device according to the present invention applies a load controlled bending moment which is constant along a length of an elongated member. The load is applied to determine the nominal strength of the elongated member from the radius of curvature of the elongated member. The load can also be increased until the elongated member fractures such that the ultimate bending moment and radius of curvature are determined.

The testing device also includes a drive system which rotates the elongated member while the bending load is applied to rapidly find flaws or defects which may only appear at a particular rotational position and determine if bending stiffness is uniform about the entire diameter of the elongated member.

The present invention therefore provides a structural testing device which determines nominal strength of an elongated member through application of a constant moment along the length of the elongated member without application of concentrated shear loads directly to the member.

BRIEF DESCRIPTION OF THE DRAWINGS

The various features and advantages of this invention will become apparent to those skilled in the art from the following detailed description of the currently disclosed embodiment. The drawings that accompany the detailed description can be briefly described as follows:

FIG. 4 is a schematic view of the testing device applying a bending load to the elongated member illustrating the radius of curvature in an exaggerated fashion for illustrated purposes; and FIG. 5 is a schematic view of another testing device with a rotational drive system which rotates the elongated member while the bending load is applied to detect flaws which may only appear at a particular rotational position of the elongated member.

DETAILED DESCRIPTION OF THE DISCLOSED EMBODIMENT

Figure 1:
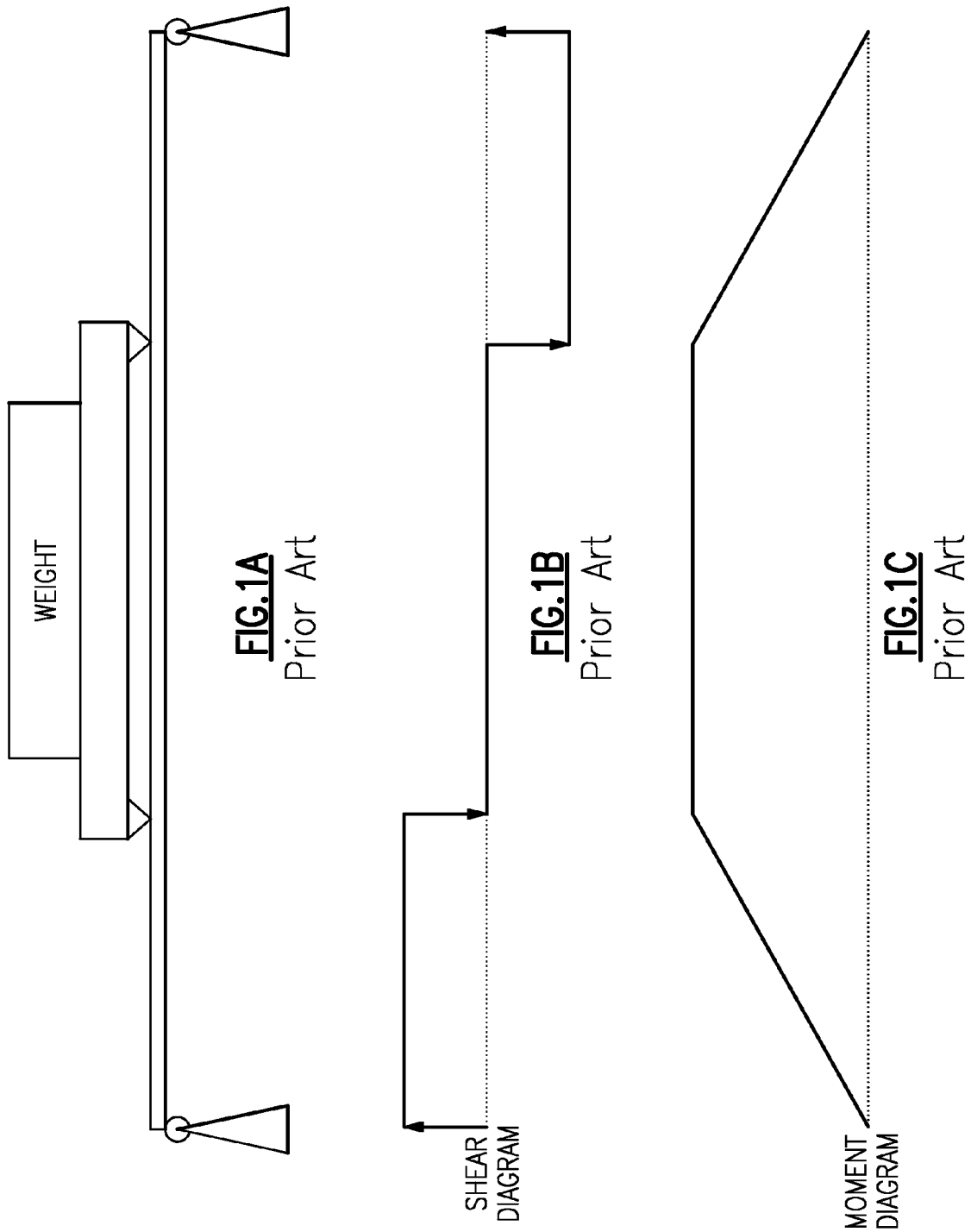
FIG. 1A is a schematic view of a PRIOR ART point testing device.
FIG. 1B is a graphically representation of a shear diagram provided by the schematic view of a PRIOR ART point testing device of FIG. 1A.
FIG. 1C is a graphically representation of a moment diagram which illustrates the non-constant moment provided by the schematic view of a PRIOR ART point testing device of FIG. 1A.
Figure 2:
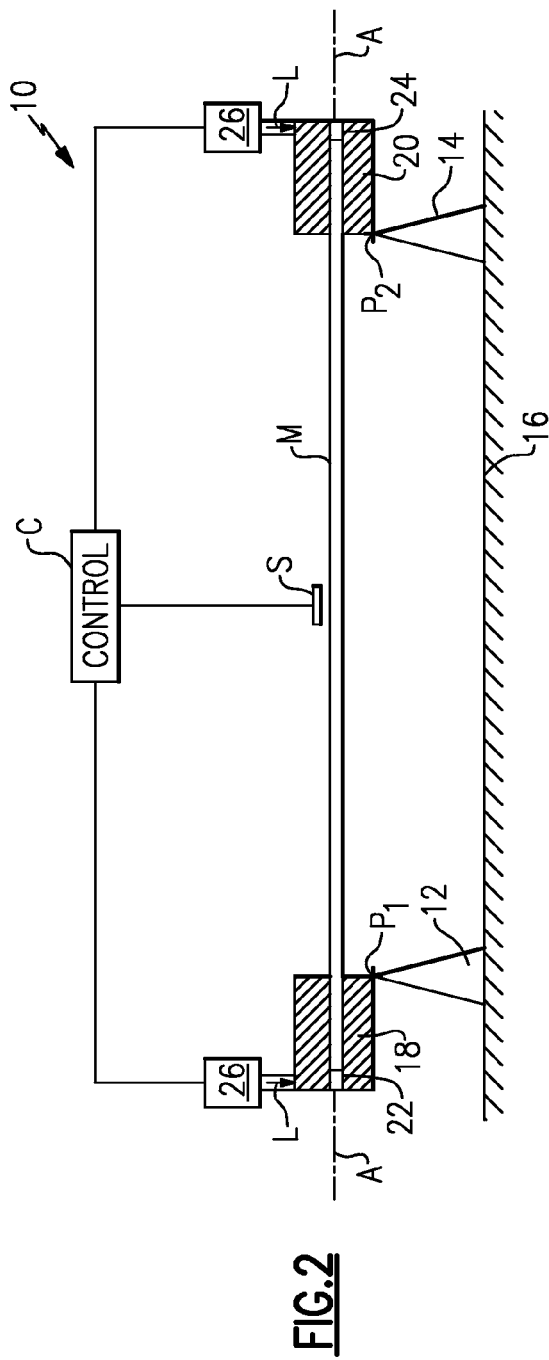
FIG. 2 is a schematic view of a testing device which applies a load controlled bending moment which is constant along a length of an elongated member to be tested.

FIG. 2 schematically illustrates a testing device 10 which applies a load controlled bending moment which is constant along a length of an elongated member M which is to be tested. The elongated member M may take various forms but is typically a thin wall hollow metallic or composite shaft or tube as well as other solid elongated members such as rods. Still other elongated members may also be tested including beams and members which are non-circular in cross-section.

The testing device 10 generally includes a first support 12 and a second support 14 which both rest on a support surface 16. A first holder 18 rests upon the first support 12 and a second holder 20 rests on the second support 14. The first holder 18 pivots upon the first support 12 about a first pivot axis P1 and the second holder 20 pivots upon the second support 14 about a second pivot axis P2. It should be understood that various pivot systems may be utilized to define the pivot axes P1, P2.

The first holder 18 and the second holder 20 include a respective opening 22, 24 which receives the elongated member M in a sliding relationship. That is, each opening 22, 24 is sized to receive the elongated member M such that the elongated member M is closely held but may slide therethrough along an axis A.

Figure 3:
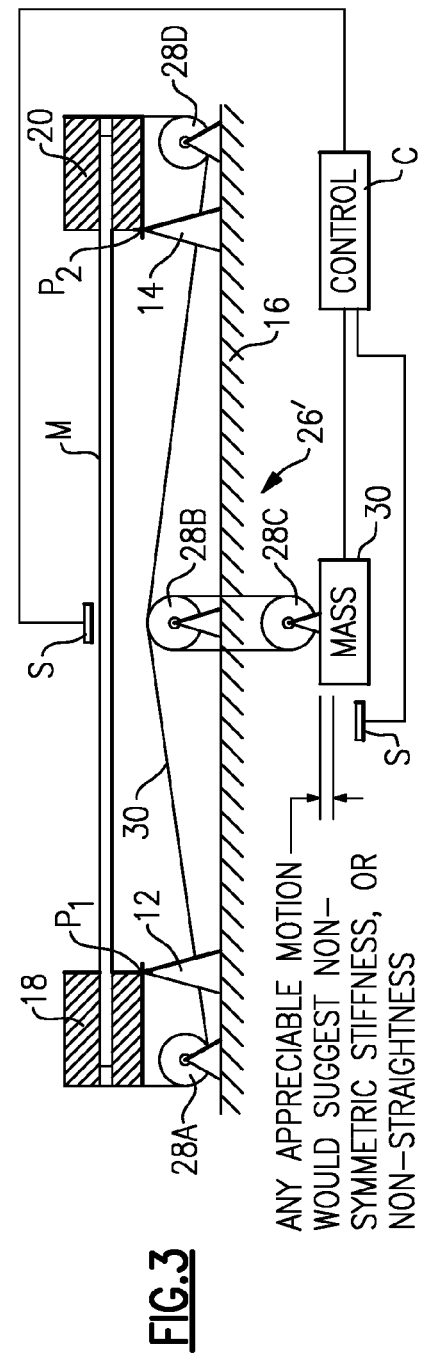
FIG. 3 is a schematic view of another testing device which applies a load controlled bending moment which is constant along a length of an elongated member to be tested.

Each holder 18, 20 is subjected to a bending load (illustrated schematically by arrow L applied through an actuator system 26 such as a pneumatic actuator, hydraulic actuator or a mass application system (FIG. 3). It should be understood that various actuator systems, load cells or such like may be utilized to apply the load.

The load L is applied to generate a bending moment which results in a radius of curvature of the elongated member M about the pivot axes P1, P2 (FIG. 4). The radius of curvature (illustrated in an exaggerated form in FIG. 4) is measured by a sensor system S (illustrated schematically) and the nominal strength of the elongated member M is determined by a controller C (illustrated schematically).

Referring to FIG. 3, the mass application system 26' in the illustrated embodiment may include a system of pulleys 28A-28D. A cable 30 affixed to the first holder 18 passes around pulley 28A, around pulley 28B, around pulley 28C, then back around pulley 28B. Pulley 28C is generally below pulley 28B relative the support surface 16. The cable 30 changes direction around pulley 28B to extend around pulley 28D where the cable 30 is affixed to the second holder 20. A mass 30 is attached to pulley 28C such that an equal load is applied to the first holder 18 and the second holder 20 through the mass application system 26'.

The load applied by the mass 30 through the mass application system 26' may result in a radius of curvature of the elongated member M about the pivot axes P1, P2 (FIG. 4). It should be understood that various mass application pulley systems and the like may be usable with the present invention. Notably, in addition to measurement of the radius of curvature of the elongated member M curvature, any appreciable motion of the mass may alternatively or additionally be measured by the sensor system S to readily indicate non-symmetric stiffness or non-straightness.

Under a non-destructive proof test scenario, a predetermined load is applied and the radius of curvature of the elongated member M under the predetermined load is calculated to detect a flaw. That is, the predetermined load is applied such that if the radius of curvature remains below a predetermined value, the elongated member has successfully passed the test. Such testing is readily applied to an elongated member M of significant length which is continuously supplied through the holders 18, 20 so that a predetermined length of the elongated member is tested in an essentially continuous manner as the elongated member M passes therethrough. A continuous supply or transit of the elongated member M through the holders 18, 20 facilitates the test of discrete segments of the elongated member M. The discrete segment is that segment which is instantaneously between the holders 18, 20. Such testing is particularly applicable during manufacture, for example, along an assembly line in which lengths of elongated material M are communicated thereby.

Under a destructive test scenario, the load L is increased until the elongated member fractures or buckles, at which time the ultimate bending moment and radius of curvature is readily determined. That is, the elongated member is tested to failure. The structural member M stress and strain at various axial and radial positions may thereafter be determined as generally understood.

Referring to FIG. 5, each holder 18, 20 further includes a bearing 32 which permits the elongated member M to rotate therein in response to a drive system 34. The drive system 34 rotates the elongated member M while the bending load is applied to rapidly find flaws or defects which may only appear at a particular rotational position of the elongated member M. Such testing readily facilitates determination of whether the bending stiffness is uniform about the entire diameter of the elongated member M.

Although particular step sequences are shown, described, and claimed herein, it should be understood that steps may be performed in any order, separated or combined unless otherwise indicated yet still benefit from the present invention.

The foregoing description is exemplary rather than defined by the limitations within. Many modifications and variations of the present invention are possible in light of the above teachings. The disclosed embodiments of this invention have been disclosed, however, one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A constant moment testing device for an elongated member comprising:
   a first support;
   a second support;
   a first holder pivotable relative said first support, said first holder having a first opening which defines a first perimeter which completely surrounds a cross-section of the elongated member to receive the elongated member along an axis;
   a second holder pivotable relative said second support, said second holder having a second opening which defines a second perimeter which completely surrounds the cross-section of the elongated member to receive the elongated member along the axis;
   an actuator system to apply a load to said first holder and said second holder, said actuator system includes a mass application system; and
   a controller operable to determine a radius of curvature of the elongated member relative said axis.

2. The testing device as recited in claim 1, where said first perimeter and said second perimeter are circular.

3. The testing device as recited in claim 1, where said first perimeter and said second perimeter are rectilinear.

4. The testing device as recited in claim 1, wherein said first perimeter is defined completely around said first axis and said second perimeter is defined completely around said second axis.

5. The testing device as recited in claim 1, wherein said first perimeter defines a closed perimeter and said second perimeter defines a closed perimeter.

6. A constant moment testing device for an elongated member comprising:
   a first support;
   a second support;
   a first holder pivotable relative said first support, said first holder having a first opening which defines a first perimeter which completely surrounds a cross-section of the elongated member to receive the elongated member along an axis;
   a second holder pivotable relative said second support, said second holder having a second opening which defines a second perimeter which completely surrounds the cross-section of the elongated member to receive the elongated member along the axis;
   a bearing within each of said first holder and said second holder to rotationally support the elongated member;
   an actuator system to apply a load to said first holder and said second holder; and
   a drive system to rotate the elongated member within the said first holder and said second holder about the axis while said actuator system applies said load to said first holder and said second holder; and
   a controller operable to determine a radius of curvature of the elongated member relative said axis.

7. A method of structural strength testing an elongated member comprising the steps of:
   (A) transiting an elongated member through a first holder having a first opening which defines a first perimeter which completely surrounds a cross-section of the elongated member to receive therethrough a section of the elongated member along an axis and a second holder having a second opening which defines a second perimeter which completely surrounds the cross-section of the elongated member to receive therethrough a section of the elongated member along an axis to test discrete segments of the elongated member;
   (B) rotating the elongated member within the first holder and the second holder about the axis while applying a load to the first holder and the second holder; and
   (C) determining a radius of curvature of the elongated member relative said axis.

8. A method as recited in claim 7, wherein said step (B) further comprises:
(a) applying a load of a predetermined constant value.

9. A method as recited in claim 7, wherein said step (B) further comprises:
(a) applying a load of increasing value.

10. A method as recited in claim 7, wherein said step (B) further comprises:
(a) applying a load of increasing value until the elongated member fails.

11. A method of structural strength testing an elongated member comprising the steps of:
(A) locating an elongated member within a first holder and a second holder along an axis, the first holder and the second holder each having an opening that respectively define a perimeter which completely surrounds a cross-section of the elongated member;
(B) rotating the elongated member within the first holder and the second holder about the axis while applying a load to the first holder and the second holder; and
(C) determining a radius of curvature of the elongated member relative said axis.

12. A method of structural strength testing an elongated member comprising the steps of:
(A) transiting an elongated member through a first holder having a first opening which defines a first perimeter which completely surrounds a cross-section of the elongated member to receive therethrough a section of the elongated member along an axis and a second holder having a second opening which defines a second perimeter which completely surrounds the cross-section of the elongated member to receive therethrough a section of the elongated member along an axis to sequentially test discrete segments of the elongated member;
(B) applying a load to the first holder and the second holder;
(C) rotating the elongated member within the first holder and the second holder about the axis during said step (B); and
(D) determining a radius of curvature of the elongated member relative the axis.

13. A method as recited in claim 12, wherein said step (B) further comprises:
(a) applying a load of a predetermined constant value.

14. A method as recited in claim 12, wherein said step (B) further comprises:
(a) applying a load of increasing value.

15. A method as recited in claim 12, wherein said step (B) further comprises:
(a) applying a load of increasing value until the elongated member fails.

* * * * *